United States Patent [19]

Gharibian

[11] Patent Number: 5,449,068

[45] Date of Patent: Sep. 12, 1995

[54] SURGICAL BLADE REMOVER

[75] Inventor: Noel Gharibian, Glendale, Calif.

[73] Assignee: Devon Industries, Inc., Chatsworth, Calif.

[21] Appl. No.: 138,415

[22] Filed: Oct. 18, 1993

[51] Int. Cl.$^6$ .................. B23P 19/04; B65D 85/00
[52] U.S. Cl. ............................ 206/355; 29/239
[58] Field of Search ............... 29/239, 278; 206/355, 206/359, 363, 370

[56] References Cited

U.S. PATENT DOCUMENTS

| | | | |
|---|---|---|---|
| 3,172,316 | 3/1965 | Grieshaber . | |
| 4,120,397 | 10/1978 | Neumann | 206/370 |
| 4,180,162 | 12/1979 | Magney | 206/359 |
| 4,270,416 | 6/1981 | Thompson | 206/359 |
| 4,318,473 | 3/1982 | Sandel . | |
| 4,395,807 | 8/1983 | Eldridge et al. | 206/355 |
| 4,746,016 | 5/1988 | Pollak et al. | 206/359 |
| 4,903,390 | 2/1990 | Vidal et al. | 206/355 |
| 5,088,173 | 2/1992 | Kromer et al. | 206/355 |

OTHER PUBLICATIONS

Devon Sharps Counting and Disposal Systems Brochure-No Date.

*Primary Examiner*—Jimmy G. Foster
*Attorney, Agent, or Firm*—Lyon & Lyon

[57] ABSTRACT

Apparatus for safely and conveniently removing a blade from a surgical scalpel, and for disposing of used blades. The preferred embodiment includes an aperture through which the blade may be inserted into a container. The aperture is defined by parallel guide walls. A first and second shoulder project from one guide wall, and a third shoulder projects from the other guide wall. An angled blade deflector is disposed in the interior of the container, behind the aperture. Insertion of the scalpel blade into the aperture and against the angled blade deflector pushes the blade against the first and second shoulders, which causes the blade to deform and separate slightly from the handle and to engage the third shoulder. This third shoulder holds the rear of the blade within the aperture, so that manual withdrawal of the handle from the aperture detaches the blade from the handle, leaving the detached blade within the container for easy disposal.

11 Claims, 3 Drawing Sheets

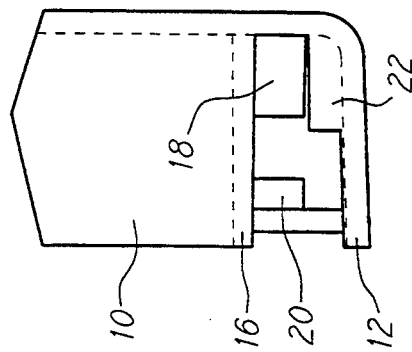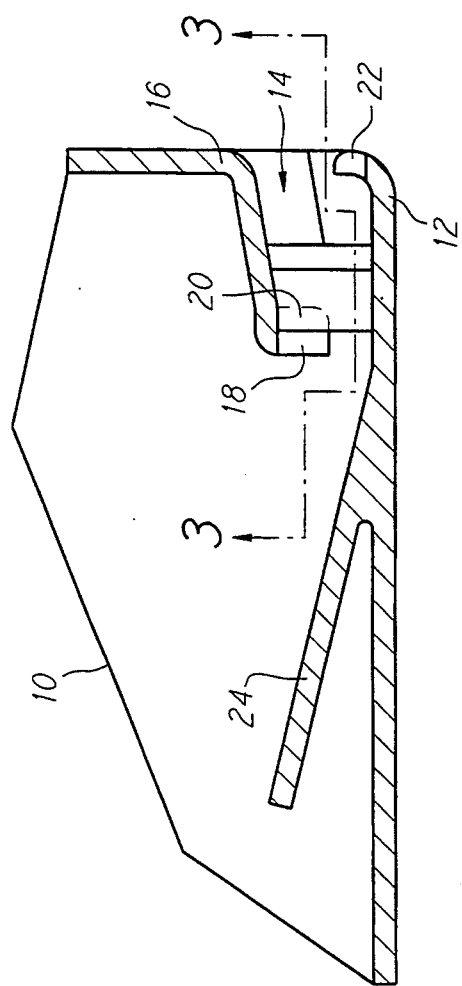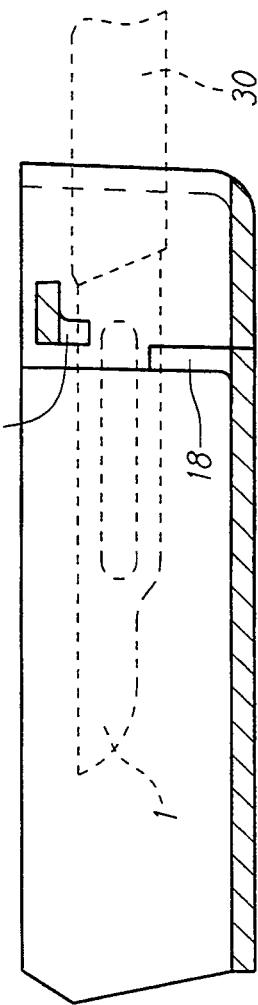

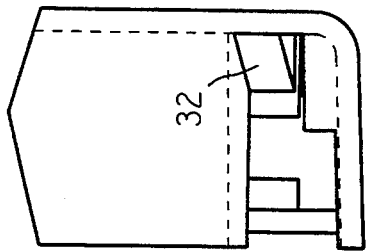
FIG. 7.
FIG. 8.
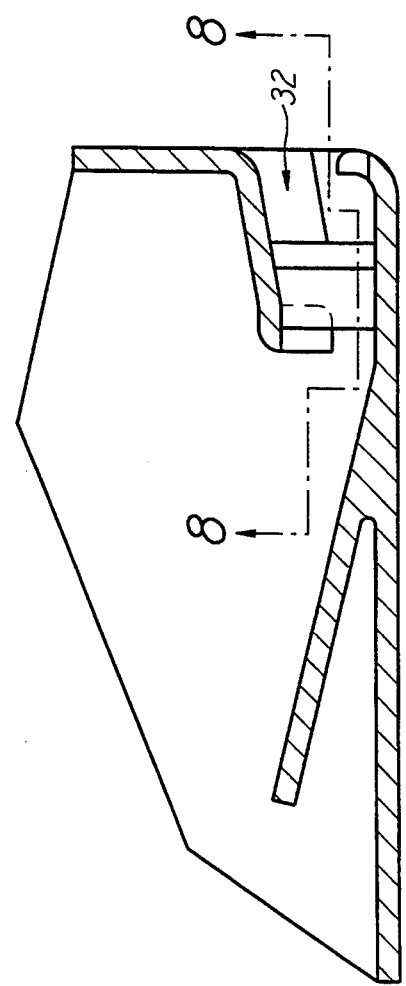
FIG. 6.
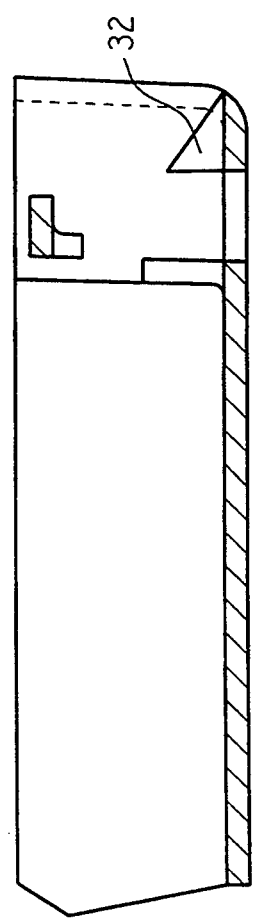

SURGICAL BLADE REMOVER

BACKGROUND OF THE INVENTION

This invention relates to a surgical blade remover, for safely removing used surgical blades from various surgical instrument handles. This invention also relates to a disposable container for safely disposing of contaminated surgical blades and sharps.

Typical surgical knives or scalpels comprise a disposable blade which can be removably attached to a handle portion. During and after surgical procedures, the used blade portion is removed from the handle and disposed of. The handle portion may then be cleaned and sterilized and used again in a subsequent surgical procedure, by attaching a new blade.

In order to minimize injury to medical personnel handling and using these types of sharp surgical instruments, as well as to the patient undergoing the surgery, several important safety needs must be met. For example, the medical personnel must be able to safely and easily remove the blades from the handle without injuring themselves in the process. Additionally, the medical personnel must be able to accurately account for all blades that are used and removed during surgery, in order to insure that no contaminated blades remain in the patient or in the operating room. Further, the medical personnel must be able to safely dispose of used blades so that the blades cannot accidentally cause injury to others.

A typical surgical blade contains a tapered slot on the lower portion of the blade which engages a raised portion on the side of the handle to securely attach the blade to the handle. The wider portion of the blade slot is disposed near the rearward edge of the blade, and the narrower portion of the slot is disposed near the forward edge of the blade, with the forward edge of the blade being the cutting edge. On the handle, the raised portion has a rounded front and rear with a groove on both sides. To attach the blade to the handle, the slot is aligned with the forward end of the raised portion of the handle, so that the slot engages the groove on the raised portion of the handle. The blade is slid down the raised portion of the handle until the rearward (wider) end of the slot is aligned with the rearward end of the raised portion. Because of the taper in the blade slot, as the blade is slid along the raised portion of the handle, it is frictionally secured in the groove. The rearward end of the blade is then pressed down against the handle until it engages the rearward portion of the raised portion and the blade is flush with the handle. This positioning of the rearward end of the blade against the raised portion prevents the blade from being slid in the opposite direction and thereby becoming disengaged from the handle. When the blade is in position on the handle, the edges of the blade, including the sharpened cutting edge, project beyond the contours of the handle.

To remove the blade from the handle, medical personnel typically would disengage the rear portion of the slot of the blade from the rearward end of the raised portion by lifting it away from the handle using a hemostat or similar tool, and then slide the blade in the opposite direction along the raised portion. However, in order to disengage the rear portion of the handle from the raised portion to permit this sliding, the blade would have to be bent within its elastic limits. This bending involves a high degree of danger, since as soon as the blade slot disengaged from the groove of the raised portion, the elastic force created in the blade tends to cause the blade to snap away from and be propelled from the handle. This can cause injury or result in the blade being temporarily lost in the operating room.

Accordingly, the need has arisen for a safe and convenient means for removing surgical blades from the handles which minimizes the risk of injury during removal.

U.S. Pat. No. 4,318,473 to Sandel, incorporated herein by reference, discloses a surgical blade removal and disposal device in which a blade and handle are inserted through a guide so that the rear of the blade is in contact with two shoulders, and the forward end of the blade is under an abutment. To remove the blade from the handle, the handle is urged downward against the shoulders, which bows the blade, thereby disengaging the rear end of the blade from the rear face of the raised portion of the handle. The handle is then pulled from the guide means while a wall and stop restrain the blade, thereby disengaging the blade from the handle.

While this known surgical blade removal device achieves safe removal of blades from knives and other surgical instruments, the prying or levering motion of the handle required on the part of medical personnel to operate it limits its flexibility.

SUMMARY OF THE INVENTION

Accordingly, the present invention overcomes the disadvantages described above, as well as others apparent to those in the art, by providing a safe, effective and convenient means for removing surgical blades from handles which minimizes the risk of injury during removal, while being flexible and simple to operate.

The surgical blade remover according to the present invention preferably includes a container having an aperture into which the scalpel and attached scalpel blade are inserted in a linear direction. The scalpel is pushed forward into the aperture, until it comes into contact with a blade deflector advantageously formed as a ramp, which pushes the forward end of the blade off-line at an angle from the linear direction of insertion. Shoulders located on the aperture wall exert a force on the rearward end of the blade in the opposite direction. The forces exerted by the blade deflector and the shoulders create a bending force which disengages the rearward portion of the blade from the handle. The scalpel is then withdrawn from the aperture in the same linear direction. While the scalpel is being pulled out of the aperture, the rearward end of the blade, which is no longer in secure frictional contact with the handle, engages a shoulder on the blade remover which holds the blade against the withdrawing action and thereby slides the blade off of the handle.

The novel and advantageous features of the present invention may be understood by one skilled in the art by reference to the following drawing figures and the detailed discussion below.

BRIEF DESCRIPTION OF THE DRAWINGS

FIG. 1 is a top plan view fragment of a surgical blade remover according to the present invention;

FIG. 2 is an end view fragment from one end of the surgical blade remover;

FIG. 3 is a section view fragment of the surgical blade remover taken along line 3—3;

FIG. 6 is a plan view fragment of an alternative embodiment of the blade remover;

FIG. 7 is an end view fragment thereof; and

FIG. 8 is a section view fragment thereof.

DETAILED DESCRIPTION OF THE PREFERRED EMBODIMENT

To more clearly illustrate the novel and advantageous features of the present invention, a conventional surgical scalpel and scalpel blade will first be briefly described with reference to FIG. 5. Although reference will be made here to scalpel blades, the present invention may also be used to remove and dispose other surgical implements that are mounted on handles in a similar fashion such as needles, saw blades and the like.

Figure 5:
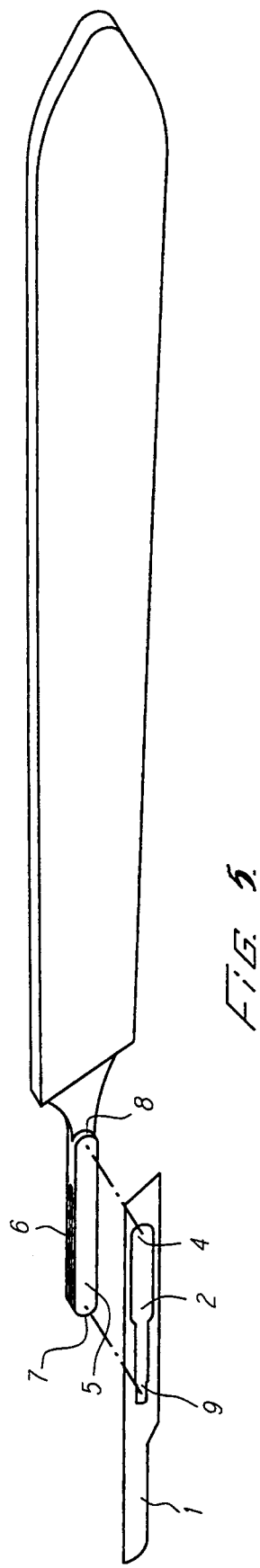
FIG. 5 shows a conventional surgical scalpel and blade.

A typical scalpel blade 1 is illustrated in FIG. 5. The blade has a keyed slot 2 with a narrow portion 9 and a wider portion 4 toward the rearward end of the blade. A scalpel handle has a raised portion 5 with grooves 6 on either side. The raised portion 5 has rounded front and rear faces 7 and 8. The raised portion is generally wider than the narrow portion 9 of the blade slot, but fits through the wider portion 4 of the slot to allow attachment and removal of the blade onto the handle, and the grooves 6 are deep enough to permit narrow portion 9 of the blade to engage the grooves 6 and be held on the raised portion. When the blade is in its normal position on the handle, the rear face 8 engages the rear edge of the blade slot, which prevents the blade from moving along the slot 2 on the grooves 6. Additionally, the rear edge of the blade may abut a surface of the handle to help prevent movement of the blade. Since the blade is somewhat wider than the handle, the edges of the blade project beyond the handle when the blade has been attached.

Manual removal of the blade requires the rear end of the blade to be lifted away from the handle to disengage the rear face 8 of the raised portion from the rear edge of the blade slot to permit the blade to slide along grooves 6 to the left in FIG. 5. However, removing the blade by hand runs the risk of injury, since it is relatively easy for the users' fingers to accidentally slide along the sharpened edge of the blade. Further, the lifting of the rear end of the blade away from the handle deforms the blade slightly, and creates an elastic tension in the blade. When the blade is slid free from the grooves of the raised portion, this tension may cause the blade to suddenly snap off of the handle, increasing the risk of injury or loss of the blade within the operating room.

The present invention therefore provides an improved device for removing of a blade from the handle. A preferred embodiment of the present invention is shown generally in FIG. 1.

The present invention includes a container 10 generally comprising an enclosed polyhedral container, such as shown in U.S. Pat. No. 4,318,473. The container 10 is used for storing used surgical sharps, such as scalpel blades or suture needles, for disposal. In a preferred embodiment, the container has a hinged lid which may be closed and securely fastened for disposal. The lid may be fastened closed by a snap feature or any other means known in the art. It should be understood that the discussion herein and the depiction in the drawing figures of the precise shape and dimensions of the container, as well as the precise means by which the lid is securely fastened, are illustrative only and are not essential to the present invention.

In one embodiment of the invention, the container may be formed of molded plastic. The precise material used to form the container is not essential to the present invention, provided that the material is of sufficient strength and thickness to prevent the blades or needles stored inside from penetrating the container walls.

During surgery, the lid may be kept open, so that medical personnel can view the contents of the box in order to keep count of the number of blades or other sharps that have been used and removed. The floor or bottom of the box may be provided with a magnetic surface so that blades and other metal sharps placed into the container will not accidentally fall out of it. Alternatively, the bottom of the box may be provided with a rubber or foam surface, for the same reason. When the surgery is completed, medical personnel can inspect the contents of the container, and when all used sharps are accounted for, can close and secure the lid and dispose of the entire container.

Referring to FIGS. 1-3, the blade remover comprises an aperture or opening 14 disposed in a wall of the container, into which a surgical scalpel and blade can be inserted in order to remove the blade. The aperture 14 is defined by a first guide wall 16 and a second guide wall 12 opposite the guide wall 16. The guide wall 16 may be formed so that the aperture tapers slightly, so that aperture 14 becomes narrower as it progresses into the container. In a preferred embodiment, the guide wall 16 may be formed at an angle of 10 degrees from parallel, relative to the opposing wall 12 of the container.

When a scalpel and blade are inserted into the aperture 14 of the blade remover, the guide wall 16 and the walls of the container guide the scalpel into the interior of the container. A short distance into the aperture 14 along the guide wall 16 (i.e., at a distance from the exterior wall of the container), shoulders 18 and 20 are disposed projecting from guide wall 16. Although in a preferred embodiment, this distance is 0.470 inches, the precise distance may be varied without affecting the scope or spirit of the present invention. However, the dimensions of the blade remover, including this distance, should preferably be such that a single blade remover can accommodate blades and handles of many different sizes and shapes.

Shoulders 18 and 20 may be better understood with reference to FIGS. 2 and 3. Shoulders 18 and 20 are substantially rectangular and project from guide wall 16 partially into the path of a scalpel inserted into aperture 14. However, the dimensions of shoulders 18 and 20 are such that sufficient space exists between the lower ends of shoulders 18 and 20 and the aperture wall 12 to permit the blade of a scalpel to pass therebetween. Additionally, the shoulders 18 and 20 are sufficiently narrow, and are disposed sufficiently far apart, to permit the front end of the handle portion of a scalpel to pass through the space created between the shoulders.

The shoulders 18 and 20 may be disposed on the guide wall 16 such that, when viewed from the perspective of FIG. 1 or FIG. 3, the two shoulders are located at slightly different distances from the external entrance of the aperture 14, so that the blade remover can accommodate surgical handles and blades of varying sizes and shapes, and having asymmetrical shapes, such as a typical scalpel blade illustrated in FIG. 5.

An angled blade deflector 24 is provided extending from aperture wall 12 into the interior of the container 10. In a preferred embodiment, this blade deflector 24 extends at an angle of about 13 degrees from the container wall 12, so that the blade deflector 24 forms a ramp rising from the portion of wall 12 opposite the shoulders 18 and 20 into the interior of the container 10.

A third shoulder 22 is provided on the aperture wall 12, at the external entrance of the aperture 14. Shoulder 22 comprises a substantially rectangular portion projecting from aperture wall 12 partially into the aperture 14.

In operation, a scalpel having an attached blade is inserted into aperture 14, with the raised portion of the scalpel (the portion onto which the blade slot fits when it is attached) facing aperture wall 12. The scalpel is pushed forward into the aperture 14, so that the scalpel blade passes through the space between the shoulders 18 and 20 and the aperture wall 12, and the handle of the scalpel passes through the space between shoulder 18 and shoulder 20. As the scalpel blade passes the shoulders 18 and 20, it begins to slide along the ramp formed by the blade deflector 24. The angle of the ramp pushes the blade and handle of the scalpel at an angle off-set from the direction of insertion, as the scalpel is pushed further into aperture 14. As the forward end of the scalpel travels along the incline of the ramp of the blade deflector 24, the scalpel is caused to move generally in an upward direction of the arrows 3 in FIG. 1, until the rearward portion of the blade extending beyond the handle contacts the shoulders 18 and 20. The shoulders 18 and 20 prevent the rearward portion of the blade from moving further upward as the scalpel moves further along the incline of the blade deflector 24. However, since the handle of the scalpel is narrow enough to fit between the shoulders 18 and 20, this handle continues to move upward while the blade is held against this movement by the shoulders 18 and 20. Thus, as the scalpel is further inserted into the aperture 14, and as the forward end of the scalpel continues to rise along the incline of the ramp, the shoulders 18 and 20 cause the rearward portion of the blade to separate slightly from the handle. This separation increases as the scalpel is inserted further into aperture 14 and the forward end of the blade moves further along the incline of blade remover 24, which causes the handle to move further in direction 3 between the two shoulders 18 and 20.

This separation is further increased by a bending action exerted on the forward end of the blade by the blade deflector 24, as will now be discussed. As the shoulders 18 and 20 prevent the blade from moving upward as the forward end of the blade travels along the incline of the blade deflector 24, the blade deflector 24 tends to bend the forward end of the blade about the end of the handle as the scalpel is inserted more deeply into aperture 14. This bending action operates as a torque on the blade, which increases as the scalpel is pushed further into the aperture 14 and the forward end of the blade travels further along the incline formed by blade deflector 24. The bending force applied to the forward end of the blade will deform the blade within its elastic limits, causing the rearward portion of the blade to bend away from and separate even further from the handle, until the rearward portion of the slot has disengaged from the rear face 8 of the raised portion. When this happens, the scalpel handle may be removed from the blade remover by pulling it out of aperture 14. While the scalpel handle is being pulled out of aperture 14, the rearward edge of the blade, which is no longer in secure frictional contact with the handle, will come into contact with shoulder 22, which will hold the blade against the withdrawing action of the scalpel. As the handle is then pulled further from the blade remover, the withdrawing action causes the handle to slide against the blade which is being held in place by the shoulder 22. This sliding motion causes the slot of the blade to slide along the groove on the raised portion of the handle. Thus, the pulling of the handle from the aperture 14 while the rearward portion of the blade is held in place by the shoulder 22 and the forward end of the blade is bent within its elastic limits around the handle, creates the combination of forces necessary to remove the blade from the handle. This sliding motion continues as the handle is further withdrawn from the aperture 14 until the slot of the blade has been completely freed of the groove on the raised portion of the handle. When the handle has been pulled completely from the aperture 14, the blade will have been completely disengaged from the handle and will remain in aperture 14. Thereafter, the loose blade can be transferred to the interior of the container 10 by simply tilting the container 10 until the loose blade is free of the shoulders 18 and 20 and the ramp 24.

Figure 4:
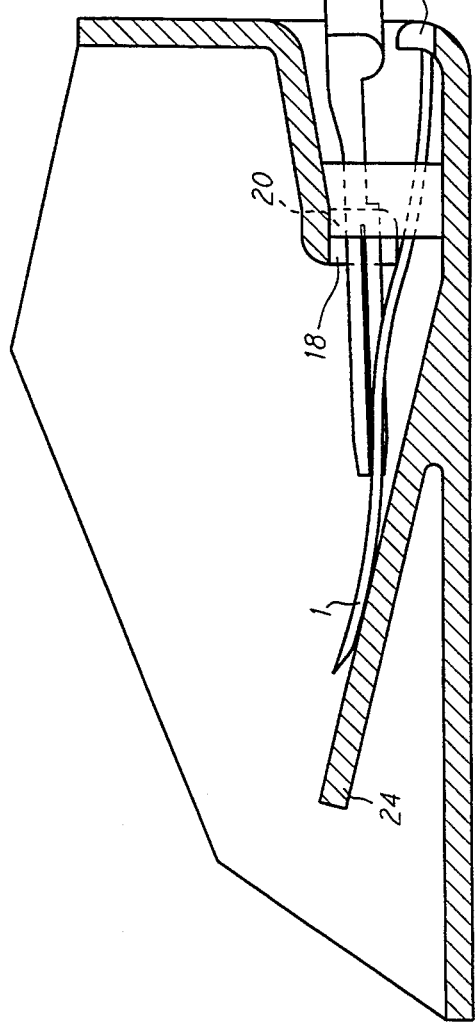
FIG. 4 shows a scalpel blade in the process of being removed from a scalpel handle by the blade remover according to the present invention.

The operation of the blade remover may be further understood by reference to FIG. 4, which depicts a conventional scalpel, indicated generally by reference numeral 30, which has been fully inserted into the blade remover of the present invention. As can be seen, the forward end of scalpel blade 1 has been elastically bent by the incline of the blade remover 24, and the shoulders 18 and 20 have caused the rearward portion of the blade 1 to separate from the handle, so that the rear edge of the blade is engaged in contact with shoulder 22. Withdrawal of the scalpel along the line indicated by arrow 34 will cause the blade 1, held within the blade remover by shoulder 22, to slide along the raised portion until it disengages from the scalpel handle.

As can be seen, the optimal dimensions of the various parts of the blade remover as herein described should be such that insertion of the scalpel into aperture 14 causes the rearward edge of the blade to engage shoulder 22 at approximately the precise moment that the rear edge of the slot has become completely disengaged from the rear face 8 of the raised portion of the handle. This insures that during withdrawal of the scalpel, when the separation between the rearward portion of the blade and the handle becomes smaller as the torque created by the shoulders 18 and 20 and the blade deflector 24 is lessened, the rear edge of the slot is not permitted to re-engage the rear face 8 before the rear edge of the blade can engage the shoulder 22, as would occur if the distance between the shoulder 22 and the base of the blade deflector 24 is too large. In a preferred embodiment, satisfactory performance is achieved by disposing the base of the blade deflector 24 approximately one-half inch from the shoulder 22 along wall 12.

The blade remover as described above therefore permits medical personnel to remove a blade from a scalpel or surgical knife by simply inserting the blade end of the scalpel into aperture 14 until the blade deflector 24 and shoulders 18 and 20 bend the blade, thereby deforming it within its elastic limits so that shoulder 22 engages the rearward edge of the blade, and then withdrawing the scalpel while the shoulder 22 holds the blade in place against the withdrawing action. The entire process is performed quickly and easily by simply inserting the blade into the apparatus on a straight line and pushing it forward, and then removing the handle on the same straight line. By performing this simple motion, the blade is removed from the handle and remains in the interior of the container 10, for easy disposal.

In another embodiment of the present invention depicted in FIGS. 6, 7, and 8, a shoulder ramp 32 may be provided on one edge of the aperture 14, to facilitate proper insertion of the scalpel blade into the surgical blade remover. The shoulder ramp 32 may comprise a projecting portion angled as shown in FIG. 8, so that a surgical blade and scalpel improperly inserted into aperture 14 will slide along the angled surface and into proper alignment in the aperture 14 relative to the shoulders 18 and 20.

Although this particular invention has been described in detail with particular reference to the exemplary embodiment, various modifications may be made to it by one skilled in the art which will fall within the scope and spirit of the present invention as set forth in the appended claims.

I claim:

1. A surgical blade remover, comprising:
   a guide wall;
   an opposing wall parallel to said guide wall with said guide wall and said opposing wall forming an aperture between them;
   first and second shoulders projecting from said guide wall into said aperture;
   a third shoulder projecting from said opposing wall into said aperture;
   a blade deflector on said opposing wall; and
   a side wall perpendicular to said guide wall and said opposing wall, and a shoulder ramp on said side wall projecting into said aperture.

2. The surgical blade remover of claim 1, wherein said blade deflector is an angled ramp formed on an interior portion of said container.

3. The surgical blade remover of claim 2, wherein said blade deflector is angled at an angle of about thirteen degrees from said interior portion of said container.

4. The surgical blade remover of claim 1, wherein said first and second shoulders are spaced apart so as to permit the handle portion of a surgical scalpel to pass therebetween while the shoulders engage the portion of the scalpel blade projecting beyond the scalpel handle.

5. The surgical blade remover of claim 4, wherein said first and second shoulders are located approximately one-half inch behind the exterior of the aperture.

6. The surgical blade remover of claim 1, further comprising a shoulder ramp disposed on said aperture to facilitate insertion of said surgical instrument into said blade remover.

7. The surgical blade remover of claim 1, wherein the blade deflector is an angled ramp extending from said opposing wall and disposed such that a surgical blade inserted into said aperture will contact the incline of said angled ramp.

8. The surgical blade remover of claim 7, wherein said angled ramp is disposed on said opposing wall such that the base of the ramp is located on said opposing wall at a location substantially opposite the location of the first and second shoulders on the guide wall.

9. A surgical blade remover for removing a blade disposed on a raised portion of a handle, said blade having a forward edge, a rearward edge, and a rear portion engaging a rear face of said raised portion, the surgical blade remover comprising:
   a guide wall;
   an opposing wall substantially facing, parallel to and fixed with respect to said guide wall so that an aperture is formed therebetween;
   an angled blade deflector disposed on said opposing wall and projecting into the aperture so as to deflect the forward edge of a blade inserted into said aperture;
   first and second shoulders disposed on said guide wall and substantially fixed with respect to the opposing wall and projecting into said aperture, said first and second shoulders disposed to exert a separating force against said deflection on the rear portion of a blade inserted into said aperture, said separating force exerted in a direction substantially opposite the direction of deflection of the forward edge of the blade so as to separate said rear portion of the blade from the rear face of the raised portion;
   a third shoulder disposed on said opposing wall for engaging the rearward edge of the blade after separation from the handle caused by the separating force and holding said blade against withdrawal from the aperture.

10. The surgical blade remover of claim 9, further comprising a container body adjacent the aperture and disposed to receive the blade after removal from the handle.

11. The surgical blade remover of claim 10, wherein said blade deflector and said first and second shoulders are disposed in the interior of said container, so that a blade removed by the blade remover remains in the container body.

* * * * *